(12) United States Patent
Stössel et al.

(10) Patent No.: US 7,414,133 B2
(45) Date of Patent: Aug. 19, 2008

(54) PALLADIUM AND PLATINUM COMPLEXES

(75) Inventors: Philipp Stössel, Frankfurt (DE); Ingrid Bach, Bad Soden (DE); Hubert Spreitzer, Viernheim (DE)

(73) Assignee: Merck Patent GmbH

( * ) Notice: Subject to any disclaimer, the term of this patent is extended or adjusted under 35 U.S.C. 154(b) by 637 days.

(21) Appl. No.: 10/534,173

(22) PCT Filed: Nov. 4, 2003

(86) PCT No.: PCT/EP03/12279

§ 371 (c)(1),
(2), (4) Date: May 6, 2005

(87) PCT Pub. No.: WO2004/041835

PCT Pub. Date: May 21, 2004

(65) Prior Publication Data

US 2006/0071206 A1    Apr. 6, 2006

(30) Foreign Application Priority Data

Nov. 8, 2002   (DE) ............................... 102 51 986

(51) Int. Cl.
*C07F 15/00* (2006.01)
*H01L 51/54* (2006.01)

(52) U.S. Cl. ............................ 546/2; 549/3; 549/206; 313/504; 257/40; 528/423; 526/265

(58) Field of Classification Search ............... 546/2; 549/3, 206; 313/504; 257/40; 528/423; 526/265
See application file for complete search history.

(56) References Cited

U.S. PATENT DOCUMENTS

| 4,539,507 | A | 9/1985 | VanSlyke et al. |
|---|---|---|---|
| 5,151,629 | A | 9/1992 | VanSlyke |
| 5,621,131 | A | 4/1997 | Kreuder et al. |
| 5,679,760 | A | 10/1997 | Mullen et al. |
| 5,763,636 | A | 6/1998 | Kreuder et al. |
| 6,653,438 | B1 | 11/2003 | Spreitzer et al. |
| 2004/0138455 | A1 | 7/2004 | Stossel et al. |

FOREIGN PATENT DOCUMENTS

| EP | 0 707 020 | 4/1996 |
|---|---|---|
| EP | 0 842 208 | 5/1998 |
| EP | 0 894 107 | 2/1999 |
| EP | 1 028 136 | 8/2000 |
| EP | 1 191 613 | 3/2002 |
| EP | 1 238 981 | 9/2002 |
| WO | WO-92/18552 | 10/1992 |
| WO | WO-02/15645 | 2/2000 |
| WO | WO-00/22026 | 4/2000 |
| WO | WO-02/068435 | 9/2002 |

*Primary Examiner*—P. Nazario Gonzalez

(57) ABSTRACT

The invention relates to novel metallo-organic compounds which are phosphorescence emitters. Such compounds can be used as active components (functional materials) in a range of different applications which form part of the electronics industry in the broadest sense. The inventive compounds are described by the formulae (1), (1a), (2), (2a), (3), (4), (5), (6), (7) and (8).

27 Claims, No Drawings

PALLADIUM AND PLATINUM COMPLEXES

RELATED APPLICATIONS

This application is a national stage application (under 35 U.S.C. 371) of PCT/EP2003012279 filed Nov.4, 2003 which claims benefit to German application 102 51 986.2 filed Nov. 8, 2002.

Organometallic compounds, especially compounds of the $d^8$ metals, will find use as functional components in the near future as active components (=functional materials) in a series of different types of application which can be classed within the electronics industry in the broadest sense.

The organic electroluminescent devices based on organic components (for a general description of the construction, see U.S. Pat. No. 4,539,507 and U.S. Pat. No. 5,151,629) and their individual components, the organic light-emitting diodes (OLEDs), have already been introduced onto the market, as demonstrated by the car radios having organic displays from Pioneer. For the polymeric OLEDs (PLEDs) too, a first product in the form of a relatively small display (in a shaver from PHILIPS N.V.) has become available on the, market. Further products of this type will shortly be introduced. In spite of this, distinct improvements are still necessary here for these displays to provide real competition to the currently market-leading liquid crystal displays (LCDs) or to overtake them.

A development in this direction which has emerged in recent years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4-6].

For theoretical reasons relating to the spin probability, up to four times the energy efficiency and performance efficiency are possible using organometallic compounds as phosphorescence emitters. Whether this new development will establish itself firstly depends strongly upon whether corresponding device compositions can be found which can utilize these advantages (triplet emission=phosphorescence compared to single emission=fluorescence) in OLEDs too. The essential conditions for practical use are in particular a long operative lifetime, a high stability against thermal stress and a low use and operating voltage, in order to enable mobile applications. In addition, there has to be efficient chemical access to the corresponding organometallic compounds. Of particular interest in this context are organopalladium and -platinum compounds. Especially taking into account the cost of palladium and platinum, it is of crucial importance here that efficient access to the corresponding derivatives is enabled.

The present invention provides 5'-mono-, 5',5"-di-halo-functionalized mono- and bis-ortho-metalated organo-palladium and organoplatinum compounds (according to compounds (1), (1a) or (2), (2a)), 5',5"-mono- or di-halo-functionalized bis-ortho-metalated bridged organopalladium and organoplatinum compounds (according to compound (3) and (4)), and cationic, uncharged or anionic 5'-mono-halo-functionalized mono-ortho-metalated organopalladium and organoplatinum compounds (according to compound (5), (6), (7) and (8)), which will be the central key building blocks for obtaining highly efficient triplet emitters, since the halogen function can be converted to a multitude of functions with the aid of common methods described in the literature. This allows not only the covalent incorporation of these active, light-emitting centers into a multitude of polymers, but also the tailoring of the optoelectronic properties of these building blocks. For instance, starting from the structure mentioned, typical C—C bond-forming reactions (for example Stille or Suzuki coupling), or else C-heteroatom bond-forming reactions (for example, for C—N: Hartwig-Buchwald coupling, similarly also for C—O and C—P) are possible here, in order thus either to further functionalize the halogen-functionalized compounds or to use them as (co)monomers in the preparation of corresponding polymers.

5'-mono-, 5,5"-di-halo-functionalized mono- and bis-ortho-metalated organopalladium and organoplatinum compounds (according to compounds (1), (1a) or (2), (2a)), 5',5"-mono- or di-halo-functionalized bis-ortho-metalated bridged organopalladium and organoplatinum compounds (according to compound (3) and (4)) and cationic, uncharged or anionic 5'-mono-halo-functionalized mono-ortho-metalated organopalladium and organoplatinum compounds (according to compound (4), (6), (7) and (8)) have not been described to date in the literature, but their efficient preparation and availability as pure materials is of great significance for various electrooptical applications.

The closest prior art may be regarded as being the monobromination and monoiodination of a cationic ruthenium(II) complex which, in addition to the ortho-metalated 2-phenylpyridine ligand, also bears 2,2'-bipyridine ligands [C. Coudret, S. Fraysse, J.-P-Luanay, Chem. Commun., 1998, 663-664]. The brominating agent used is N-bromosuccinimide, the iodinating agent a mixture of iodobenzene diacetate and elemental iodine in a molar ratio of one to one. The isolated yield after chromatographic purification is reported as 95% in the case of bromination, and as 50% in the case of iodination.

The bromination, described by Clark et al., of ortho-metalated 2-phenylquinoline and 2,3-diphenyl-quinoxaline ligands of ruthenium(II) carbonyl chloro and osmium(II) carbonyl chloro complexes with pyridinium perbromide should also be regarded analogously. After chromatographic purification, yields of from 27% to 92% were obtained [A. M. Clark, C. E. F. Rickard, W. R. Roper, L. J. Wright, J. Organomet. Chem., 2000, 598, 262-275].

In addition, it has been shown in the application WO 02/068435 that the halogenation of octahedral homo- and heteroleptic rhodium and iridium complexes with an ortho-metalated ligand set proceeds very selectively and in good to very good yields.

However, this prior art described in the abovementioned references has the following disadvantages:

(1) only the halogenation of Ru, Os, Rh and Ir complexes, but not that of Pd or Pt compounds, is described.
(2) no viable teaching is provided as to how square planar, homo- and heteroleptic palladium and platinum complexes with an ortho-metalated ligand set can be halogenated selectively on the coordinated ligand. Rather, it is known that these complexes are readily amenable to oxidative addition by halogens (L. Chassot, E. Müller, A. Zelewsky, Inorg. Chem. 1984, 23, 4249-4253) and thus, according to the prior art, change from square planar to octahedral geometry.

It has now been found that, surprisingly, the novel compounds (1), (1a), (2), (2a), according to scheme 2, are obtained starting from the bis-ortho-metalated organopalladium or organoplatinum compounds (9), (9a), (10), (10a), and that the novel compounds (3) or (4), according to scheme 3, are obtained starting from the bis-ortho-metalated, bridged organopalladium and organoplatinum compounds (11) or (12), and that the novel compounds (5), (6), (7) or (8), according to scheme 4, are obtained starting from the cationic, uncharged or anionic functionalized mono-ortho-metalated organopalladium and organoplatinum compounds (13), (14),

(15) and (16) with a halogen or interhalogen, optionally in the presence of a base and optionally of a Lewis acid, and in the presence or with subsequent addition of a reducing agent or of an organic N-halogen compound, optionally in the presence of a Brønsted acid, and in the presence or with subsequent addition of a reducing agent, or with a halogenating agent consisting of an organic O-halogen compound and a halogen $X_2$, in the presence or with subsequent addition of a reducing agent, with suitable selection of the stoichiometric ratio of the appropriate halogenating agent to the compounds (9), (10), (11), (12), (13), (14), (15) or (16) and with suitable selection of the reaction parameters such as reaction temperature, reaction medium, concentration and reaction times, reproducibly in more than 80% yield, without use of chromatographic purification processes, in some cases after recrystallization, in purities of >99% by NMR or HPLC (see Example 1-3).

The above-described process is notable particularly for several features which have not been described to date in the literature:

1) without wishing to be bound thereby to a particular theory, we suspect that the exceptional tendency of square planar palladium and platinum complexes to the oxidative addition of electrophiles, here of halogens or their analogs which transfer halogenium ions, always has the consequence that a rapid oxidative addition to the metal center occurs initially with consumption of one equivalent of halogen and formation of octahedral dihalopalladium(IV) and -platinum(IV) complexes. In a second, subsequent step, these react with further equivalents of halogen to halogenate the ligands and form octahedral dihalopalladium(IV) and -platinum(IV) complexes with a halogenated, ortho-metalated ligand set. The subsequent reduction of these octahedral dihalopalladium(IV) and -platinum(IV) complexes with a halogenated ortho-metalated ligand set then leads to the square planar palladium (II) and platinum(II) complexes with a correspondingly halogenated ligand set described here. Scheme 1 shows this reaction sequence schematically.

Scheme 1:

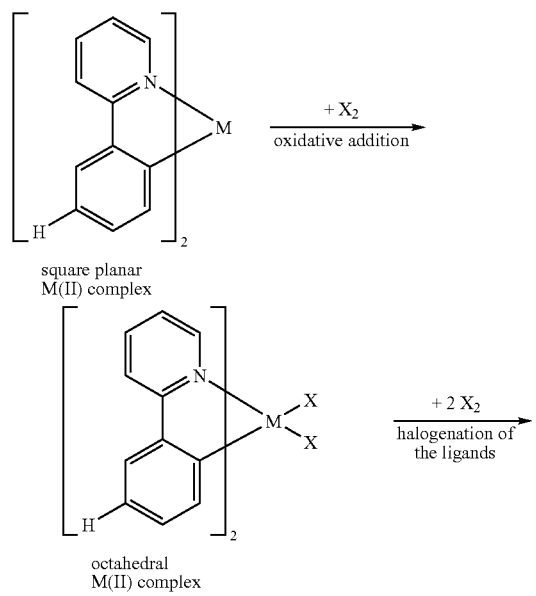

square planar
M(II) complex octahedral
M(II) complex

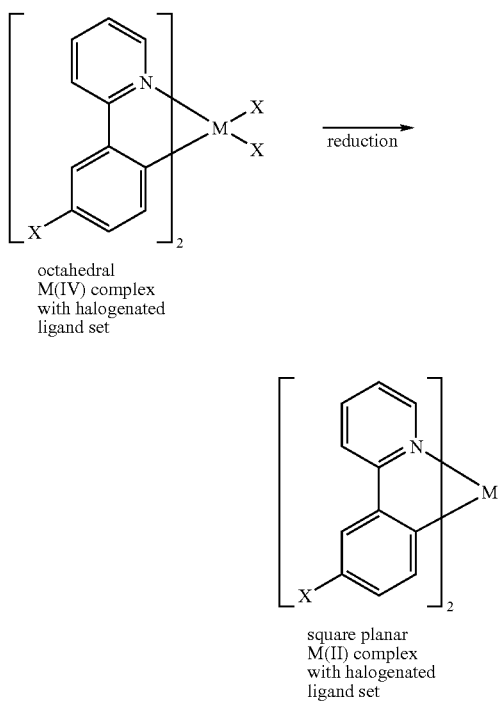

octahedral
M(IV) complex
with halogenated
ligand set square planar
M(II) complex
with halogenated
ligand set 2) The selective 5'-mono- and 5',5"-dihalogenation on square planar palladium(II) and platinum(II) complexes via the above-described dihalo-palladium(IV) and -platinum(IV) complexes is wunexpected and not known in this form. The observed high selectivity is suspected to result from the activation which is experienced by the position para to the palladium or platinum atom as a result of this atom. The unexpectedly high activity of this position compared to an electrophilic substitution, here halogenation, is utilized selectively by the use of mild halogenating agents.

3) A crucial factor for the achievement of high selectivities and high reaction rates is frequently, depending on the halogenating agent, working in the presence of an acid-binding agent which binds hydrohalic acid formed in the course of the substitution. This is a surprising finding, by which the side reactions are apparently suppressed effectively. The inventive halogenating agents accordingly comprise an acid-binding agent, such as a base, which is either an intrinsic part of the halogenating agent or is added additionally to the halogenating agent.

4) The high conversion achieved, which is reflected in the reproducibly very good yields of isolated product, is unexpected and unique for the halogenation of ortho-metalated ligands bound to metals of the nickel group.

5) The resulting compounds are obtained without costly and inconvenient chromatographic purification, in some cases after recrystallization, in very good purities of >99% by NMR or HPLC. This is essential for the use in optoelectronic components, and the utilization as valuable intermediates for the preparation of corresponding compounds.

As outlined above, the inventive compounds have not been described before and are thus novel.

The present invention thus provides the compounds (1) and (2) according to scheme 2

Scheme 2:

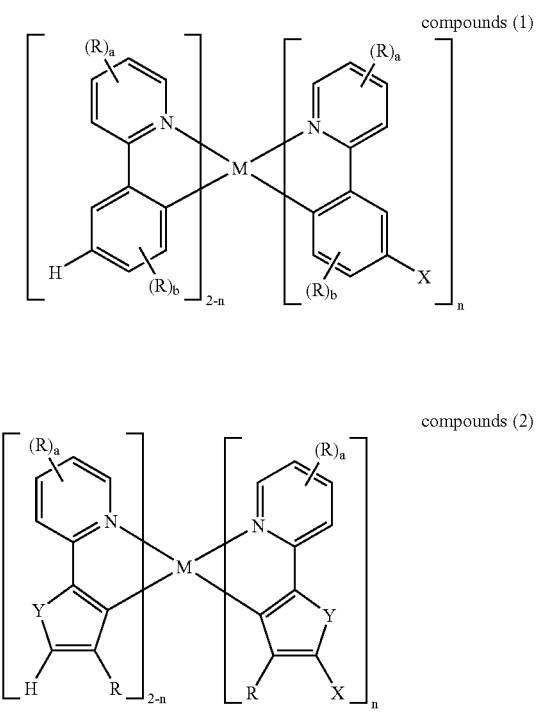

compounds (1)

compounds (2)

where the symbols and indices are each defined as follows:
M is Pd, Pt;
X is Cl, Br, I;
Y is O, S, Se, $NR^1$;
R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, —$SiR^1{}_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;
$R^1$ are the same or different at each instance and are each H or an aliphatic or aromatic hydrocarbon radical having from 1 to 20 carbon atoms;
a is 0, 1, 2, 3 or 4, preferably 0, 1 or 2;
b is 0, 1, 2 or 3, preferably 0 or 1;
n is 1 or 2.

A further embodiment of the invention relates to those Pd and Pt complexes which simultaneously have ligands of the type as in compounds (1) and those of compounds (2), i.e. mixed ligand systems. These are described by the formulae (1a) and (2a):

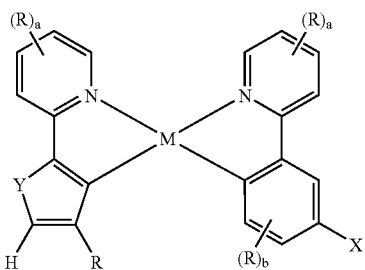

compounds (1a)

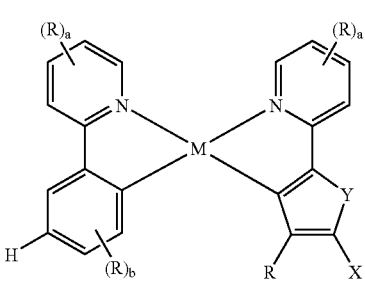

compounds (2a)

where the symbols and indices are each defined under the formulae (1) and (2).

The present invention likewise provides the compounds (3) and (4) according to scheme 3

Scheme 3:

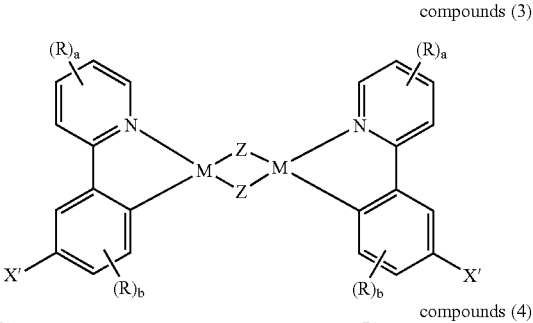

compounds (3)

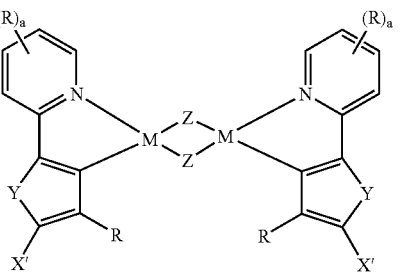

compounds (4)

where the symbols and indices are each defined as follows:
M is Pd, Pt;

X' is H, Cl, Br or I, with the proviso that at least one X' per formula is selected from Cl, Br or I;

Y is O, S, Se, $NR^1$;

Z is identically F, Cl, Br, I, $O-R^1$, $S-R^1$, $N(R^1)_2$

R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, $-SiR^1_2-$, —S—, $-NR^1-$ or $-CONR^1-$ and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

$R^1$ are the same or different at each instance and are each H or an aliphatic or aromatic hydrocarbon radical having from 1 to 20 carbon atoms;

a is 0, 1, 2, 3 or 4, preferably 0, 1 or 2;

b is 0, 1, 2 or 3, preferably 0 or 1.

The present invention likewise provides the compounds (5), (6), (7) and (8) according to scheme 4

Scheme 4:

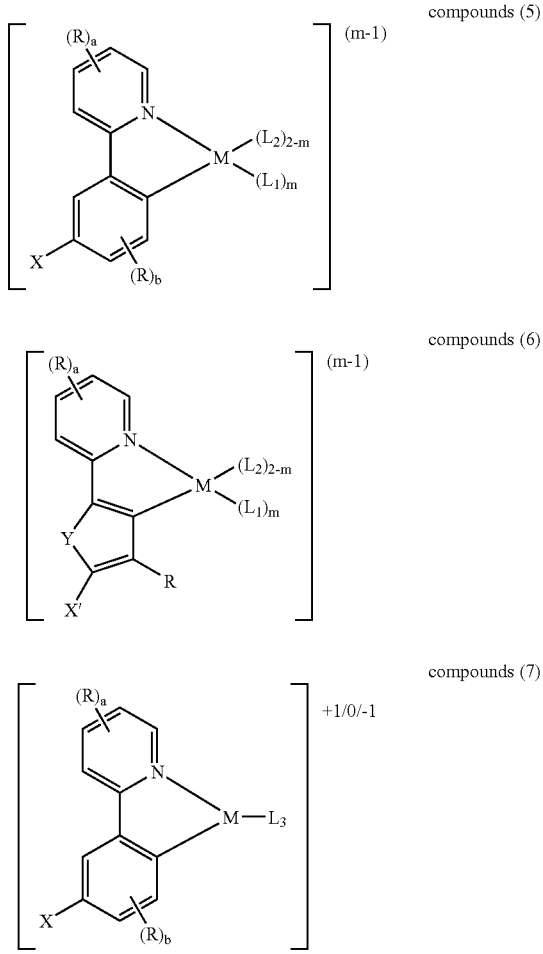

-continued

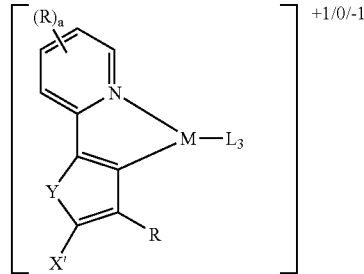

where the symbols and indices are each defined as follows:

M is Pd, Pt;

X is Cl, Br, I;

Y is O, S, Se, $NR^1$;

R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, $-SiR^1_2-$, —S—, $-NR^1-$ or $-CONR^1-$ and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

$R^1$ are the same or different at each instance and are each H or an aliphatic or aromatic hydrocarbon radical having from 1 to 20 carbon atoms;

$L_1$ is an uncharged, monodentate ligand;

$L_2$ is a monoanionic, monodentate ligand;

$L_3$ is an uncharged or mono- or dianionic bidentate ligand;

a is 0, 1, 2, 3 or 4, preferably 0, 1 or 2;

b is 0, 1, 2 or 3, preferably 0 or 1;

m is 0, 1 or 2.

Inventive uncharged, monodentate ligands $L_1$ are carbon monoxide, an isonitrile, for example tert-butylisonitrile, cyclohexylisonitrile, adamantylisonitrile, an amine, for example trimethylamine, triethylamine, morpholine, phosphines, for example trifluorophosphine, or else aliphatic, aromatic or heteroaromatic phosphines such as trimethylphoshine, tricyclohexylphosphine, dicyclohexylphenylphosphine, tri-o-tolylphosphine, tri-tert-butylphosphine, tri-phenylphosphine, tris(pentafluorophenyl)phosphine, phosphites, for example trimethyl phosphite, triethyl phosphite, arsines, for example trifluoroarsine, trimethylarsine, tricyclohexylarsine, tri-tert-butylarsine, triphenylarsine, tris(pentafluorophenyl)-arsine, stibines, for example trifluorostibine, trimethylstibine, tricyclohexylstibine, tri-tert-butylstibine, triphenylstibine, tris(pentafluorophenyl)stibine or a nitrogen-containing heterocycle, for example pyridine, pyridazine, pyrazine, triazine.

Inventive monoanionic, monodentate ligands $L_2$ are halides such as F, Cl, Br, I, cyanide, cyanate, isocyanate, thiocyanate, isothiocyanate, alkoxides, for example methoxide, ethoxide, propoxide, isopropoxide, tert-butoxide, phenoxide, a thioalkoxide, in particular, for example, methanethiolate, ethanethiolate, propanethiolate, isopropanethiolate, tert-thiobutoxide, thiophenoxide, amides, for example dimethylamide, diethylamide, diisopropylamide, carboxylates, for example acetate, trifluoroacetate, propionate, benzoate, and anionic nitrogen-containing heterocycles such as morpholide, pyrrolide, imidazolide, pyrazolide.

Inventive uncharged or mono- or dianionic, bidentate ligands $L_3$ are diamines, for example ethylenediamine, N,N,N',N'-tetramethylethylenediamine, propylenediamine, N,N,N',N'-tetramethylpropylenediamine, cis-, trans-diamihocyclohexane, cis-, trans-N,N,N',N'-tetramethyl-diaminocyclohexane, imines, for example 2[(1-(phenylimino)ethyl]pyridine, 2[(1-(2-methylphenyl-imino)ethyl]pyridine, 2[(1-(2,6-diisopropylphenyl-imino)ethyl]pyridine, 2[(1-methylimino)ethyl]pyridine, 2[(1-(ethylimino)ethyl]pyridine, 2[(1-(isopropylimino)-ethyl]pyridine, 2[(1-(tert-butylimino)ethyl]pyridine, diimines, for example 1,2-bis(methylimino)ethane, 1,2-bis(ethylimino)ethane, 1,2-(bis(isopropylimino)ethane, 1,2-bis(tert-butyl-imino)ethane, 2,3-bis(methyl-imino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenyl-imino)ethane, 1,2-bis(2,6-diisopropylphenylimino)-ethane, 1,2-bis(2,6-di-tert-butylphenylimino)ethane, 2,3-bis(phenylimino)butane, 2,3-bis(2-methylphenyl-imino)butane, 2,3-bis(2,6-diisopropylphenylimino)-butane, 2,3-bis(2,6-di-tert-butylphenylimino)butane, heterocycles containing two nitrogen atoms, for example 2,2'-bipyridine, o-phenanthroline, diphosphines, for example bis-diphenylphosphinomethane, bisdiphenyl-phosphinoethane, bis(diphenylphosphino)propane, bis(di-methylphosphino)methane, bis(dimethylphosphino)ethane, bis(dimethylphosphino)propane, bis(diethylphosphino)-methane, bis(diethylphosphino)ethane, bis(diethyl-phosphino)propane, bis(di-tert-butylphosphino)methane, bis(di-tert-butylphosphino)ethane, bis(tert-butyl-phosphino)propane, 1,3-diketonates derived from 1,3-diketones, for example acetylacetone, benzoylacetone, 1,5-diphenylacetylacetone, dibenzoylmethane, bis(1,1,1-trifluoroacetyl)methane, 3-ketonates derived from 3-keto esters, for example ethyl acetoacetate, carboxylates derived from aminocarboxylic acids, for example pyridine-2-carboxylic acid, quinoline-2-carboxylic acid, glycine, dimethylglycine, alanine, dimethylaminoalanine, salicyliminates derived from salicylimines, in particular, for example, methylsalicylimine, ethylsalicylimine, phenylsalicylimine, dialkoxides derived from dialcohols, in particular, for example, ethylene glycol, 1,3-propylene glycol, dithiolates derived from dithiols, for example 1,2-ethylenedithiol, 1,3-propylenedithiol, or heteroarylborates, for example tetrakis(1-imidazolyl)borate, tetrakis(1-pyrazolyl)-borate.

The inventive complexes (1) to (8) and (1a) and (2a) have the following advantages over the prior art:

1) As a result of the functionalization, it is simple to covalently incorporate these complexes as (co)monomers, for example, into corresponding polymers or oligomers. This may be effected either in the main chain or at the end of the main chain, or, in the case of appropriate further reactions, into the side chain of the polymer.

2) It is possible analogously by appropriate reactions to provide "defined low molecular weight complexes" which, however, have specific properties (for example high solubility, low tendency to crystallize). The incorporation into defined oligomers (for example dendrimers) is also possible effortlessly by the same reactions.

3) The access, outlined under 1) and 2), to corresponding functionalizations is of very high significance, since it is very important to integrate metal complexes either into polymers or into readily soluble low molecular weight substances.

4) It is likewise advantageous that the claimed complexes can be prepared in good purity and high yield. This is of enormous significance firstly for corresponding applications (further processing for use in electrical or electronic devices, for example OLED- or PLED-based displays) and also commercially (owing to the high raw material cost).

The present invention further provides processes for preparing the compounds (1), (2), (3), (4), (5), (6), (7) and (8) by reacting the compounds (9), (10), (11), (12), (13), (14), (15) and (16) according to scheme 5

Scheme 5:

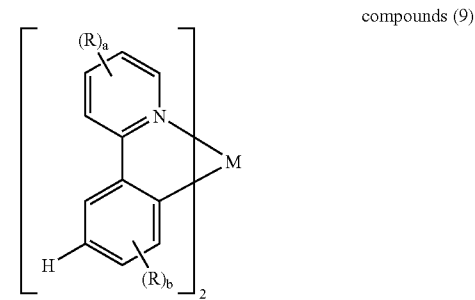

compounds (9)

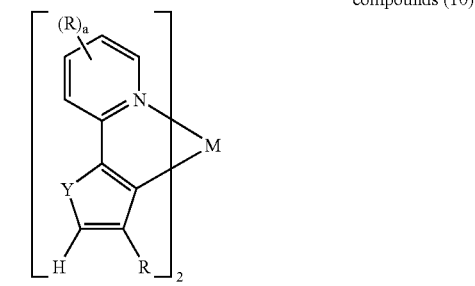

compounds (10)

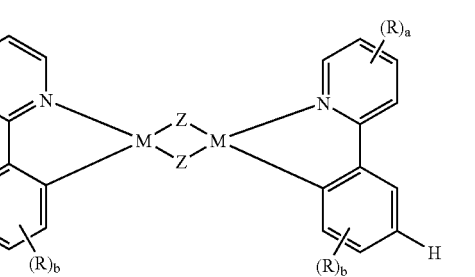

compounds (11)

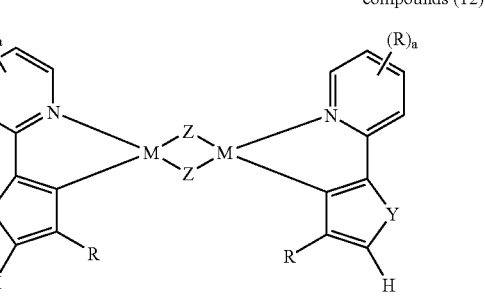

compounds (12)

-continued
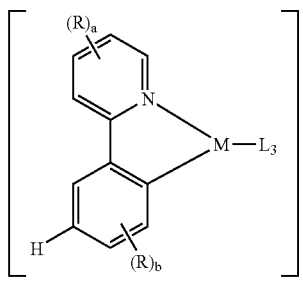
compounds (15)
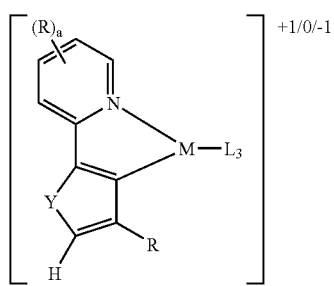
compounds (16)
in which M and the radicals and indices X, Y, Z, R, $R^1$, $L_1$, $L_2$, $L_3$, a, b and m are each as defined above with halogenating agents, followed by reducing agents.
The process according to the invention is illustrated by scheme 6:
Scheme 6:
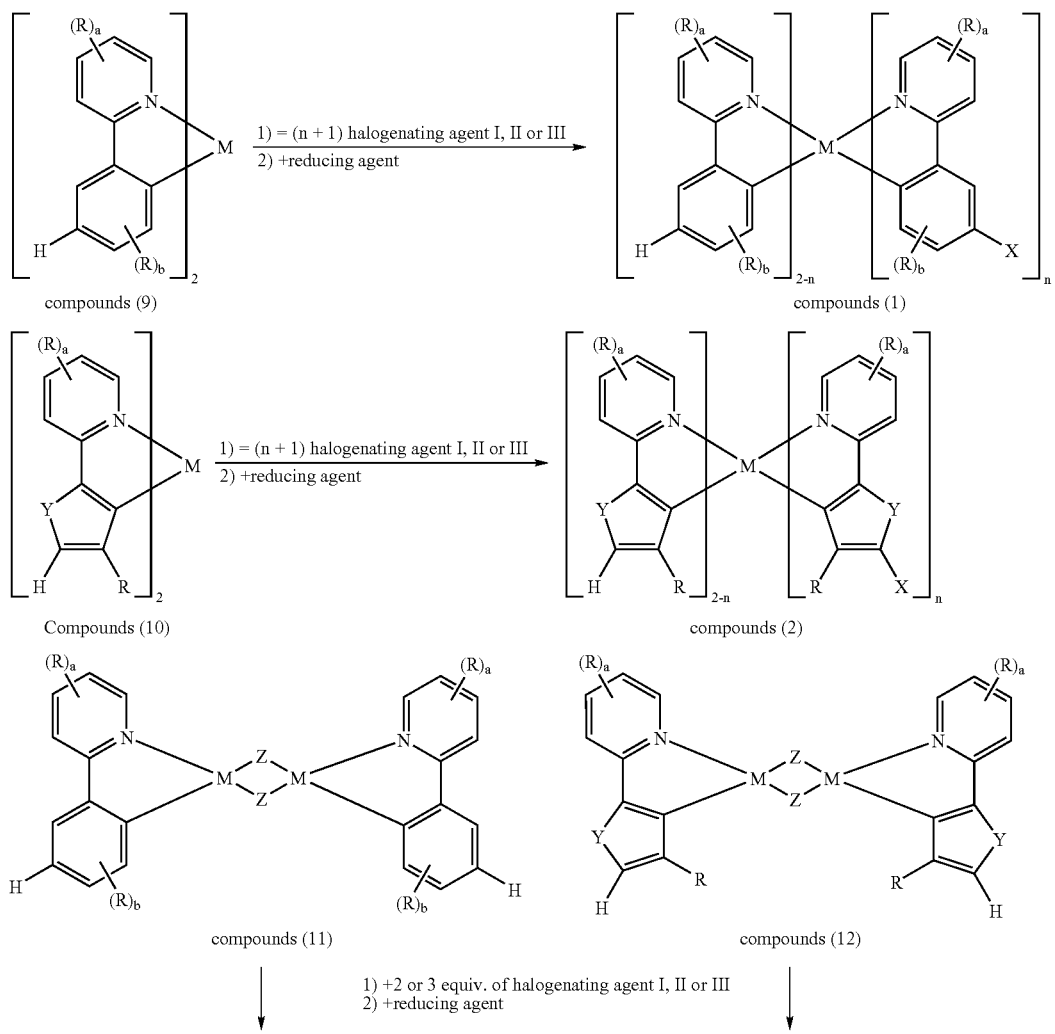

-continued

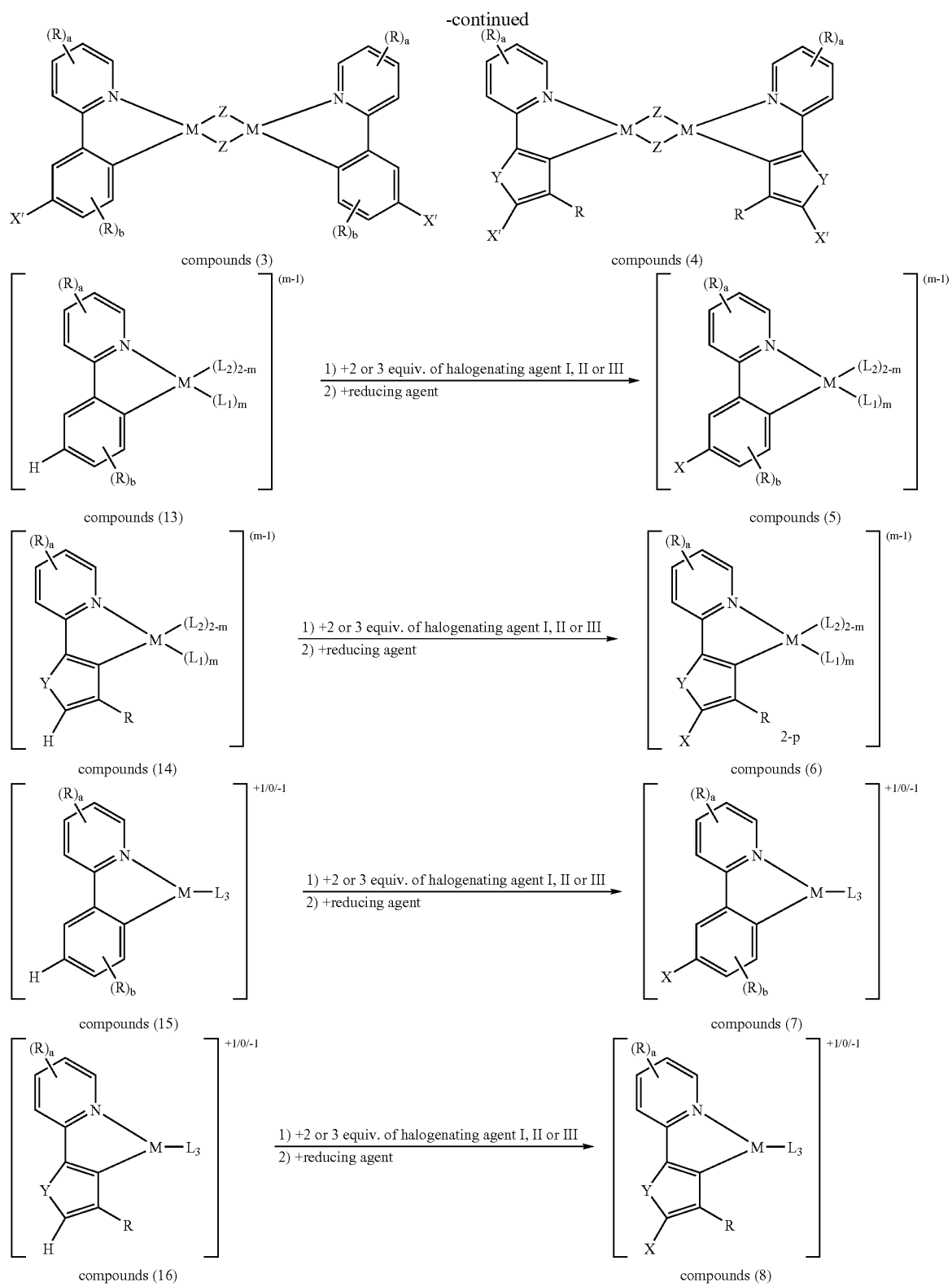

The compounds (1a) and (2a) may also be prepared analogously.

Inventive halogenating agents are the halogens $X_2$ and the interhalogens X—X and a base in a molar ratio of from 1:1 to 1:100 and optionally a Lewis acid in a molar ratio (halogen to Lewis acid) of from 1:0.1 to 1:0.0001, for example chlorine, bromine or iodine, or chlorine fluoride, bromine fluoride, iodine fluoride, bromine chloride, iodine chloride or iodine bromide, in combination with organic bases such as amines, for example triethylamine, tri-n-butylamine, duisopropylethylamine, morpholine, N-methylmorpholine and pyridine, or salts of carboxylic acids such as sodium acetate, sodium propionate, sodium benzoate, or inorganic bases such as sodium phosphate or potassium phosphate or sodium hydrogenphosphate or potassium hydrogenphosphate, sodium hydrogencarbonate or potassium hydrogencarbonate, sodium carbonate or potassium carbonate, or else organic bromine complexes such as pyridinium perbromide, in each case optionally in combination with a Lewis acid, for example boron trifluoride, boron trifluoride etherate, boron trichloride, boron tribromide, boron triiodide, aluminum trichloride, aluminum tribromide, aluminum triiodide, iron(III) chloride, iron(III) bromide, zinc(II) chloride, zinc(II) bromide, tin(IV) chloride, tin(IV) bromide, phosphorus pentachloride, arsenic pentachloride and antimony pentachloride. These halogenating agents are referred to below as halogenating agents (I).

Further inventive halogenating agents are organic N-halogen compounds, N-halocarboxamides, for example N-chloro-, N-bromo- and N-iodoacetamide, N-chloro-, N-bromo- and N-iodopropionamide, N-chloro-, N-bromo- and N-iodobenzamide, or N-halocarboximides, for example N-chloro-, N-bromo- and N-iodosuccinimide, N-chloro-, N-bromo- and N-iodophthalimide, or N-dihalosulfonamides such as N,N-dibromobenzenesulfonamide, or N-halosulrfonamide salts such as chloramine B or T.

These halogenating agents are referred to below as halogenating agents (II). In the case of the halogenating agents (II), the additive use of Lewis acids, as are listed above, for example, may likewise be advantageous.

In the case of the halogenating agents (II), the additive use of Brønsted acids, for example hydrochloric acid, hydrobromic acid, hydriodic acid, sulfuric acid or phosphoric acid, may likewise be advantageous.

Still further inventive halogenating agents are organic O-Hal compounds and halogens $X_2$ in a molar ratio of from 0.5:1 to 1:1, such as iodoaryl dicarboxylates in a molar ratio of from 0.5:1 to 1:1 with a halogen $X_2$, for example iodobenzene diacetate or bistrifluoroacetoxyiodobenzene and elemental bromine in a molar ratio of from 0.5:1 to 1:1, or iodobenzene diacetate or bistrifluoroacetoxyiodobenzene and elemental iodine in a molar ratio of from 0.5:1 to 1:1.

These halogenating agents are referred to below as halogenating agents (III).

In the process according to the invention, a stoichiometric ratio of the halogenating agents (I), (II) or (III), based on the content of active halogen, to the compounds (9), (10), (11), (12), (13), (14), (15) or (16) of 2:1 leads selectively to the compounds (1), (2) where n=1, (3), (4) where one X' is H and the other is halogen, and to the compounds (5), (6), (7) or (8). This is a surprising and unforeseeable result.

In the process according to the invention, a stoichiometric ratio of the halogenating agents (I), (II) or (III), based on the content of active halogen, to the compounds (9), (10), (11) or (12) of from 3:1 to 1000:1 leads selectively to the compounds (1), (2) where n=2, or (3), (4) where both of X' are halogen. This is a surprising and unforeseeable result.

The stoichiometric ratios described here are preferred embodiments of the present invention since they lead to uniformly substituted products. It is self-evident that slight deviations from the abovementioned ratios still lead to good to acceptable results.

According to the invention, a reducing agent is added to the reaction mixture in a molar ratio of from 1:1 to 10000:1 based on the compounds (9), (10), (11), (12), (13), (14), (15) or (16). The addition may be effected either simultaneously with the addition of the halogenating agents (I), (II) or (III), or preferably after a time delay.

Inventive reducing agents are hydrazine (hydrate) or salts thereof, for example hydrazine hydrochloride, hydrobromide, hydroiodide, hydrazine sulfate, hydrazine nitrate and hydrazine phosphate, hydroxylamine or salts thereof, for example hydroxylamine hydrochloride, hydrobromide, hydroiodide, hydroxylamine nitrate, hydroxylamine phosphate and hydroxylamine sulfate, hydroxylamine-O-sulfonic acid and hydroquinones, for example hydroquinone or tetramethylhydroquinone, alkali metal and alkaline earth metal sulfites such as lithium, sodium, potassium and magnesium sulfite, alkali metal and alkaline earth metal dithionites, for example lithium, sodium, potassium and magnesium dithionite, alkali metals and alkaline earth metals, for example lithium, sodium, potassium and magnesium, calcium, barium, and their amalgams and other corresponding alloys, transition metals such as manganese, iron, nickel and zinc, and transition metal alloys, for example Raney nickel.

According to the invention, the reduction may also be effected by dry-heating, under reduced pressure, the palladium(IV) or platinum(VI) compounds which have been formed as intermediates and isolated in substance.

Inventive reaction media are protic or aprotic, halogen-free or halogenated solvents, for example alcohols such as methanol, ethanol, propanol, butanol, polyhydric alcohols such as ethylene glycol or propylene glycol, nitriles such as acetonitrile, propionitrile or benzonitrile, ethers such as diethyl ether, THF or dioxane, aromatic hydrocarbons such as benzonitrile, nitrobenzene or chlorobenzene, N,N-dialkylamides such as dimethylformamide, dimethylacetamide or N-methylpyrrolidone, sulfoxides such as dimethyl sulfoxide, sulfones such as dimethylsulfone or sulfolane, halogenated hydrocarbons such as dichloromethane, trichloromethane, 1,1-dichloroethane, 1,2-di-chloroethane, 1,1,2,2-tetrachloroethane; preference is given to aromatic or chlorinated solvents.

According to the invention, the reaction is carried out within the temperature range from −78° C. to 150° C., preferably from 0° C. to 100° C., very preferably from 10° C. to 60° C.

According to the invention, the concentration of the palladium-containing or platinum-containing reactants, compounds (9), (10), (11), (12), (13), (14), (15) or (16), is in the range from 0.0005 mol/l to 2 mol/l, more preferably in the range from 0.002 mol/l to 0.1 mol/l.

According to the invention, the palladium-containing or platinum-containing reactants may be present dissolved or suspended in the reaction medium.

According to the invention, the reaction is carried out within from 10 minutes up to 100 hours, preferably within from 1 h to 40 h.

It is possible with the synthetic methods illustrated here to prepare the compounds (1), (1a), (2), (2a), (3), (4), (5), (6), (7) or (8), including the examples shown below.

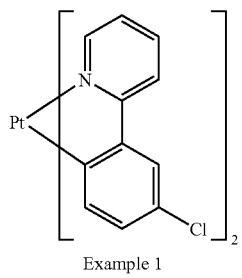
Example 1
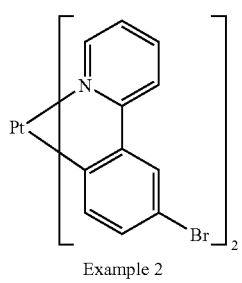
Example 2
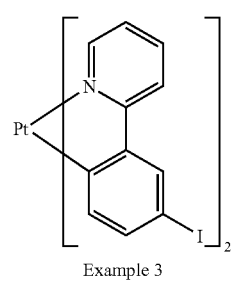
Example 3
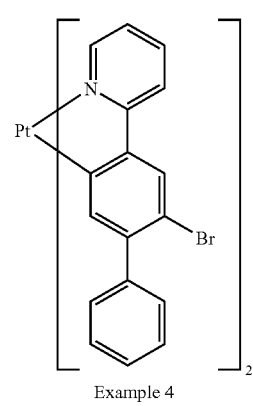
Example 4
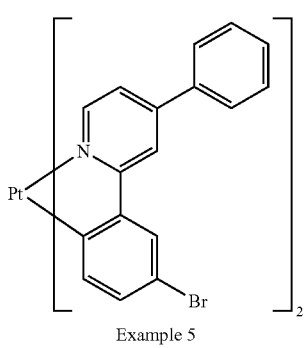
Example 5
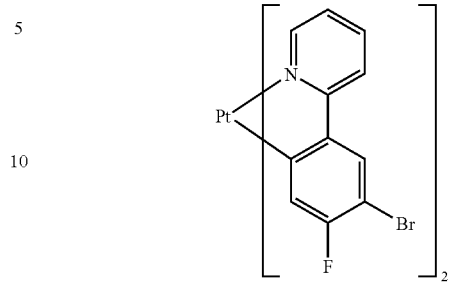
Example 6
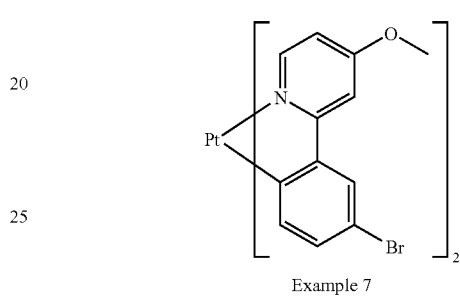
Example 7
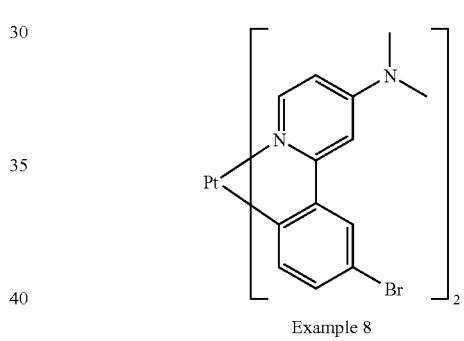
Example 8
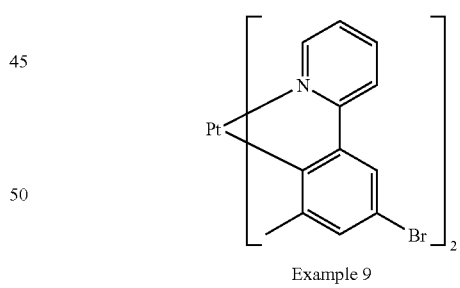
Example 9
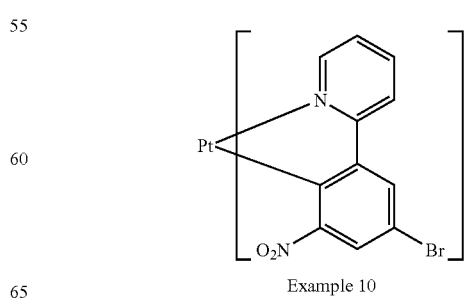
Example 10

-continued
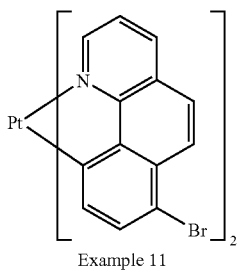
Example 11
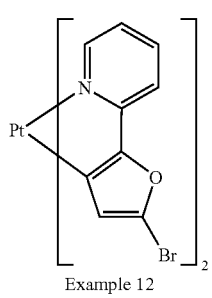
Example 12
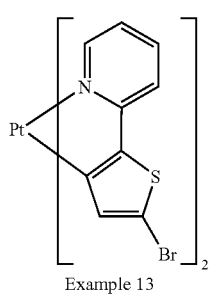
Example 13
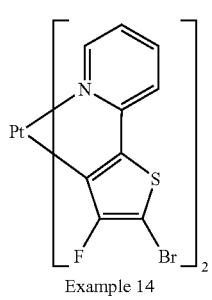
Example 14
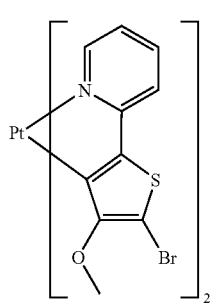
Example 15
-continued
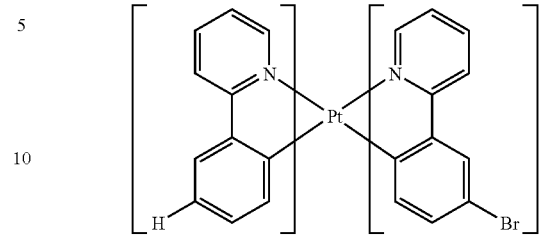
Example 16
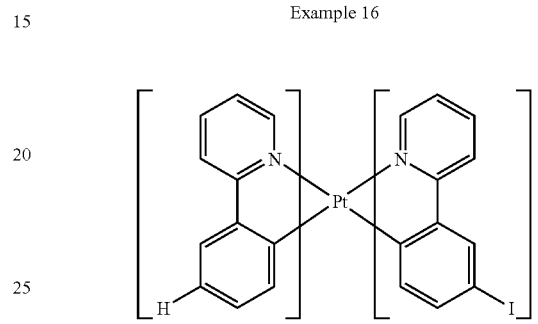
Example 17
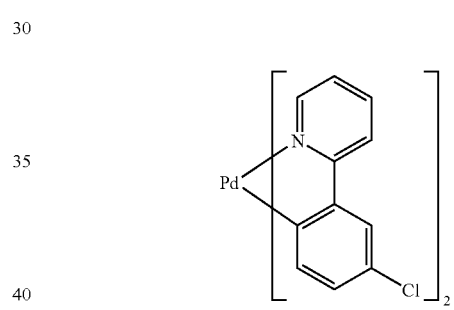
Example 18
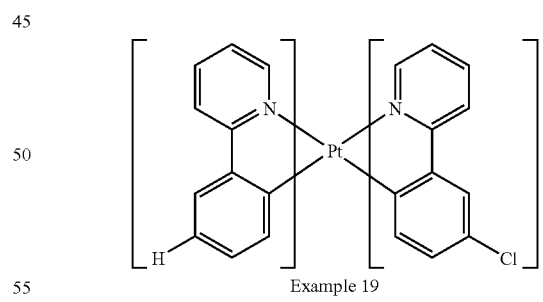
Example 19
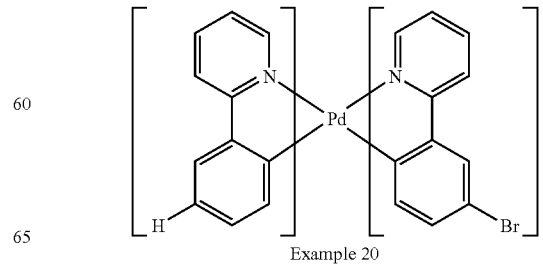
Example 20

-continued
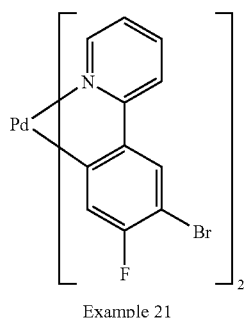
Example 21
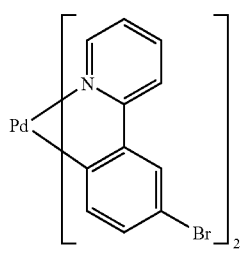
Example 22
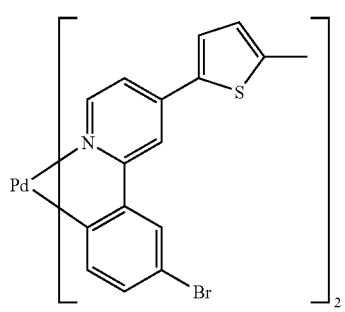
Example 23
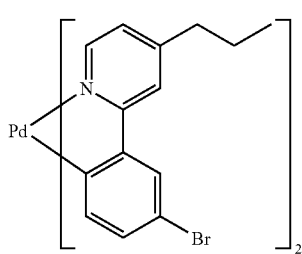
Example 24
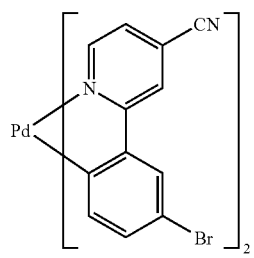
Example 25
-continued
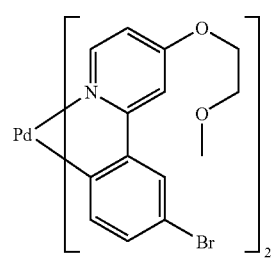
Example 26
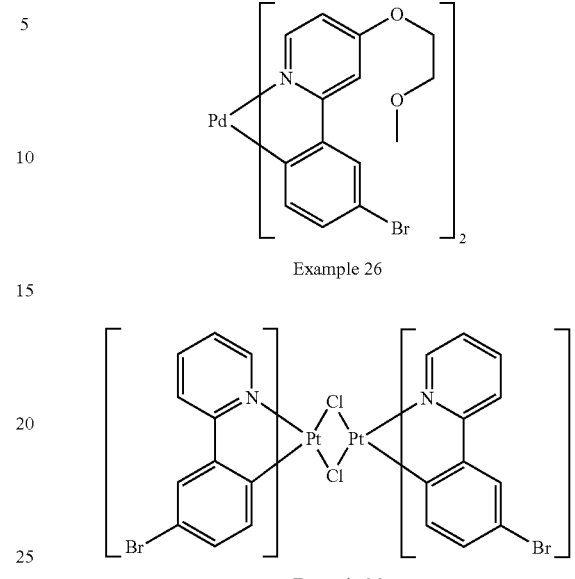
Example 26
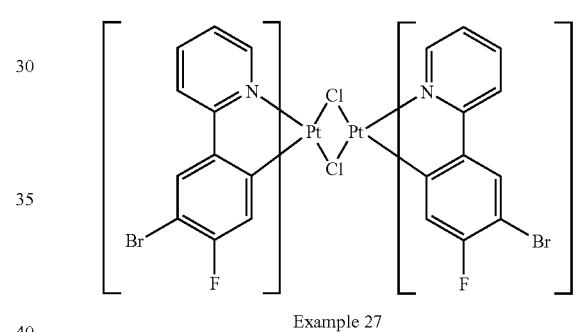
Example 27
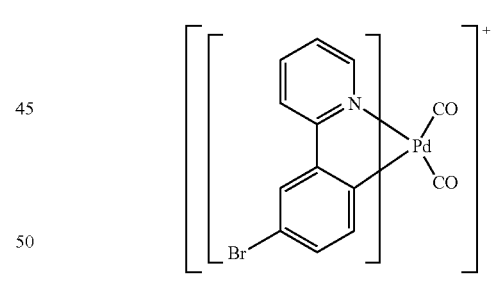
Example 28
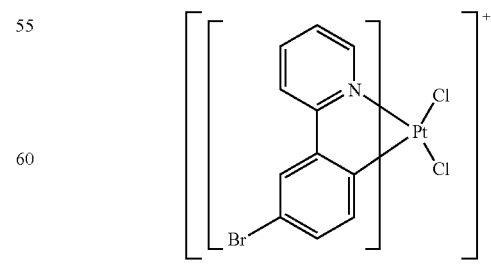
Example 29

-continued

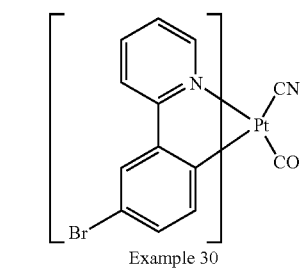

Example 30

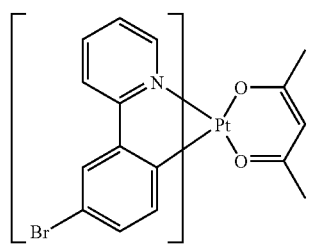

Example 31

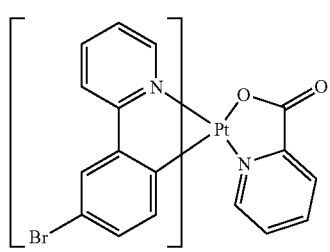

Example 32

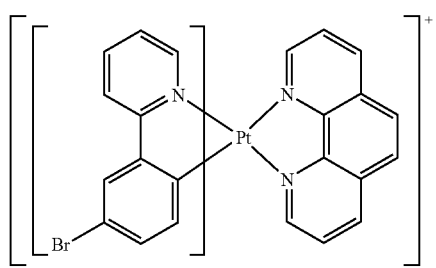

Example 33

The thus obtained inventive compounds may find use, for example, as comonomers to obtain corresponding conjugated or else semiconjugated or nonconjugated polymers. The corresponding copolymerization is preferably effected via the halogen functionality. It is thus possible to copolymerize them into polymers including soluble polyfluorenes (for example according to EP-A-842 208 or WO 00/22026), polyspirobifluorenes (for example according to EP-A-707 020 or EP-A-894 107), poly-para-phenylenes (for example according to WO 92/18552), polycarbazoles or else polythiophenes (for example according to EP-A-1 028 136).

The invention therefore further provides conjugated or semiconjugated and nonconjugated polymers containing one or more compounds of the formula (1') and/or (2')

compounds (1')

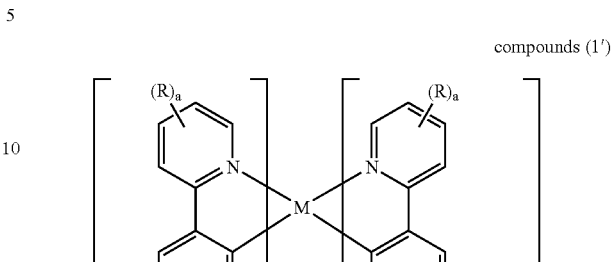

compounds (2')

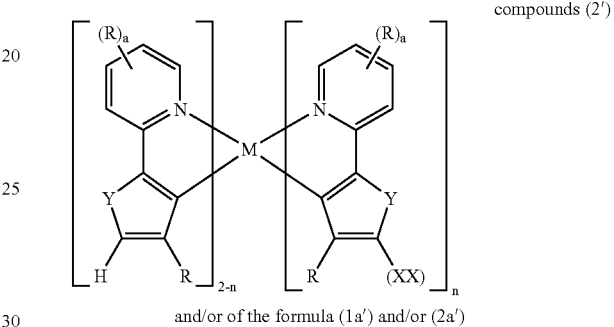

and/or of the formula (1a') and/or (2a')

compounds (1a')

compounds (2a')

and/or of the formula (3'), (4'), (5'), (6'), (7'), and/or (8')

compounds (3')

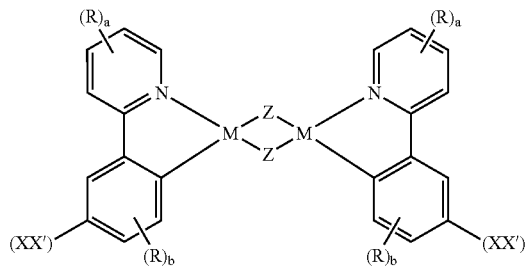

-continued

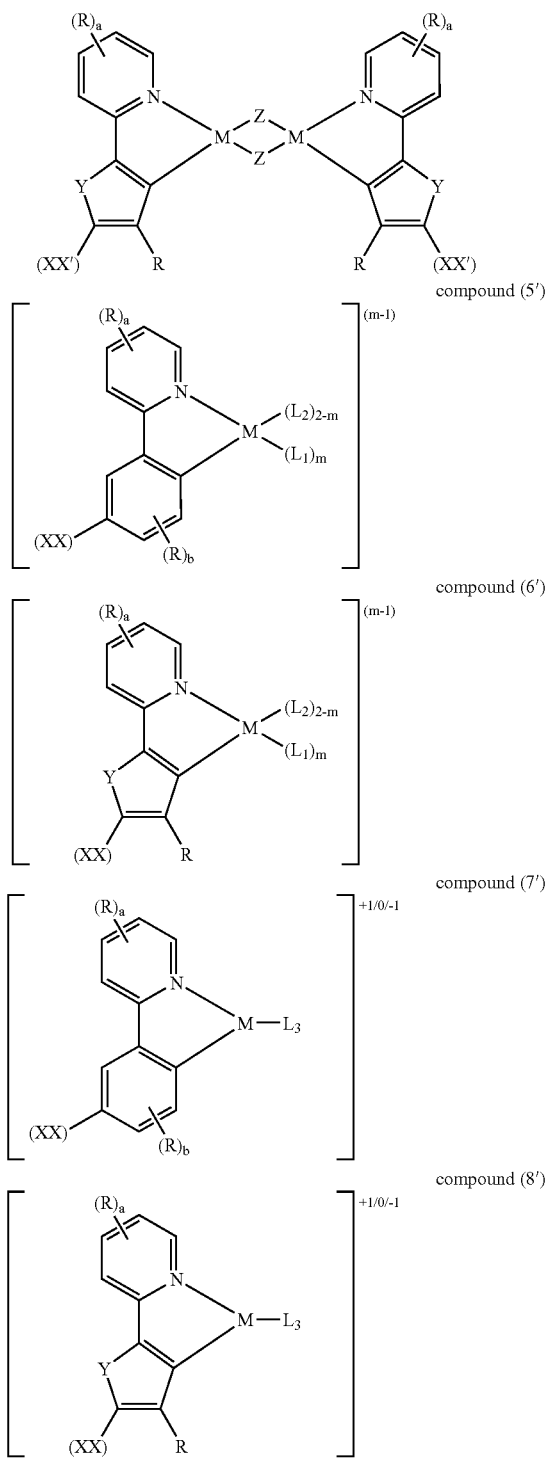

where the symbols and indices are each defined as follows:
M is Pd, Pt;
Y is O, S, Se, $NR^1$;
R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, —$SiR^1_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;
$R^1$ are the same or different at each instance and are each H or an aliphatic or aromatic hydrocarbon radical having from 1 to 20 carbon atoms;
$L_1$ is an uncharged, monodentate ligand;
$L_2$ is a monoanionic, monodentate ligand;
$L_3$ is an uncharged or mono- or dianionic bidentate ligand;
a is 0, 1, 2, 3 or 4;
b is 0, 1, 2 or 3;
m is 0, 1 or 2;
n is 1 or 2;
(XX) is a bond to the conjugated or semiconjugated or nonconjugated polymer;
(XX') is H or a bond to the conjugated or semiconjugated or nonconjugated polymer, but at least one (XX') per formula is a bond to the conjugated or semiconjugated or nonconjugated polymer.

Preference is given to conjugated, semiconjugated or nonconjugated polymers which have been obtained using one or more compounds of the formula (1), (1a), (2), (2a) and/or (3) to (8).

Conjugated or semiconjugated polymers refer to polyfluorenes, polyspirobifluorenes, poly-paraphenylenes, polycarbazoles or polythiophenes.

The conjugated or semiconjugated polymers based on polyfluorenes are preferably the polyfluorenes disclosed in EP-A-842 208 and WO 00/22026.

The conjugated or semiconjugated polymers based on polyspirobifluorenes are preferably the polyspirobifluorenes disclosed in EP-A-707 020 and EP-A-894 107.

The conjugated or semiconjugated polymers based on poly-para-phenylenes are preferably the poly-paraphenylenes disclosed in WO 92/18552.

The conjugated or semiconjugated polymers based on polythiophenes are preferably the polythiophenes disclosed in EP-A-1 028 136.

In addition, the inventive compounds may also be functionalized further by the abovementioned reaction types, for example, and thus converted to extended low molecular weight Pd or Pt complexes or defined oligomers (for example dendrimers). An example to be mentioned here is the functionalization with arylboronic acids according to Suzuki or with amines according to Hartwig-Buchwald.

The halogenated complexes or the polymers or else "extended low molecular weight complexes" or else the defined oligomers obtained therefrom may be used in electrical or electronic components, for example as light-emitting materials in organic or polymeric light-emitting diodes (OLEDs or PLEDs). However, other applications, for example in organic solar cells, organic lasers, organic photodetectors, and the like are also conceivable.

The invention therefore also provides electronic components, for example organic or polymeric light-emitting diodes (OLEDs or PLEDs), organic integrated circuits (O-ICs), organic field-effect transistors (O-FETs), organic thin-film transistors (O-TFTs), organic solar cells (O-SCs) or organic laser diodes (O-lasers), comprising one or more inventive halogenated palladium or platinum complexes or one or more inventive polymers which have been obtained using these inventive palladium or platinum complexes.

The present invention is illustrated in detail by the examples which follow, without any intention that it be restricted thereto. Those skilled in the art can prepare further inventive complexes from the descriptions without inventive activity, and employ the process according to the invention.

EXAMPLES

Synthesis of Symmetrically and Asymmaetrically Functionalized Bis-Ortho-Metalated Organopalladium or Organoplatinum Compounds:

The syntheses which follow have, unless stated otherwise, been carried out under air using commercial solvents. The reactants were purchased from Aldrich [N-chlorosuccinimide, N-bromosuccinimide, HCl, HBr, hydrazine hydrate]. Before the N-haloimides were used, the content of active halogen was determined iodometrically [analogously to: K. W. Rosenmund, W. Kuhnhenn, Ber. 1923, 56, 1262]. Bis[2-(2-pyridinyl-κN)phenyl-κC}platinum was prepared by literature methods (L. Chassot, E. Müller, A. Zelewsky, Inorg. Chem. 1984, 23, 4249-4253).

Numbering scheme for the assignment of the $^1$H NMR signals [analogously to: C. Coudret, S. Fraysse, J.-P-Launay, Chem. Commun., 1998, 663-664]:

Scheme 7:

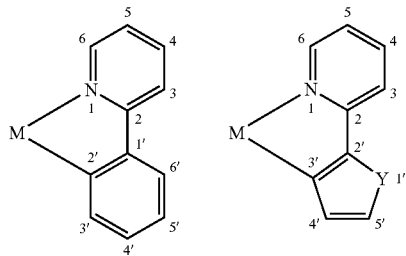

Example 1

Bis[2-(2-pyridinyl-κN)(5-chlorophenyl)-κC)]platinum(II)

588 mg (4.4 mmol) of N-chlorosuccinimide and 200 µl of conc. HCl were added under exclusion of light to an efficiently stirred solution of 504 mg (1.0 mmol) of bis[2-(2-pyridinyl-κN)phenyl-κC]platinum(II) in 200 ml of dichloromethane. The reaction mixture was stirred at room temperature for a further 20 h. Subsequently, 240 µl (5 mmol) of hydrazine hydrate and 100 ml of ethanol were added, and the mixture was heated under reflux for 2 h. After concentration to a volume of 20 ml under reduced pressure, the solution was admixed with 200 ml of ethanol. Subsequently, the microcrystalline precipitate was filtered off (P4), washed three times with 20 ml of ethanol and then dried under reduced pressure (60° C., $10^{-4}$ bar). The yield, at a purity of >99.5% by $^1$H NMR, was 501 mg, corresponding to 87.5%.

$^1$H NMR (CD$_2$Cl$_2$): [ppm]=8.91 (m, 3H), 7.91 (m, 3H), 7.83 (m, 3H), 7.57 (m, 3H), 7.43 (m, 3H), 7.37 (m, 3H), 7.09 (m, 3H).

Example 2

Bis[2-(2-pyridinyl-κN) (5-bromophenyl-κC)platinum(II)

783 mg (4.4 mmol) of N-bromosuccinimide and 170 µl of 48% by weight HBr were added under exclusion of light to an efficiently stirred solution of 504 mg (1.0 mmol) of bis[2-(2-pyridinyl-κN)phenyl-κC]platinum(II) in 200 ml of dichloromethane. The reaction mixture was stirred at room temperature for a further 20 h. Subsequently, 240 µl (5 mmol) of hydrazine hydrate and 100 ml of ethanol were added, and the mixture was heated under reflux for 2 h. After concentration to a volume of 20 ml under reduced pressure, the solution was admixed with 200 ml of ethanol. Subsequently, the microcrystalline precipitate was filtered off (P4), washed three times with 20 ml of ethanol and then dried under reduced pressure (60° C., $10^{-4}$ mbar). The yield, at a purity of >99.5% by $^1$H NMR, was 613 mg, corresponding to 92.7%.

$^1$H NMR (DMSO-d6) [ppm]=8.85 (m, 3H), 7.93 (m, 3H), 7.78 (m, 3H), 7.52 (m, 3H), 7.39 (m, 3H), 7.35 (m, 3H), 7.02 (m, 3H).

Example 3

Bis[2-(2-pyridinyl-κN) (5-bromophenyl-κC)platinum(II)

783 mg (4.4 mmol) of N-bromosuccinimide and 170 µl of 48% by weight HBr were added under exclusion of light to an efficiently stirred solution of 504 mg (1.0 mmol) of bis[2-(2-pyridinyl-κN)phenyl-κC]platinum(II) in 200 ml of dichloromethane. The reaction mixture was stirred at room temperature for a further 20 h. After concentration to a volume of 20 ml under reduced pressure, the solution was admixed with 200 ml of ethanol. Subsequently, the microcrystalline precipitate was filtered off (P4), washed three times with 20 ml of ethanol and then dried under reduced pressure (60° C., $10^{-4}$ mbar). The thus obtained platinum(IV) compound was sublimed at a temperature of from 380 to 410° C. under reduced pressure (approx. $5·10^{-4}$ mbar), in the course of which the product (the desired platinum(II) compound) was obtained as the sublimate. The yield, at a purity of >99.5% by $^1$H NMR, was 569 mg, corresponding to 86.0%.

$^1$H NMR (DMSO-d6): [ppm]=8.85 (m, 3H), 7.93 (m, 3H), 7.78 (m, 3H), 7.52 (m, 3H), 7.39 (m, 3H), 7.35 (m, 3H), 7.02 (m, 3H).

What is claimed is:

1. A compound of the formula (1) or (2)

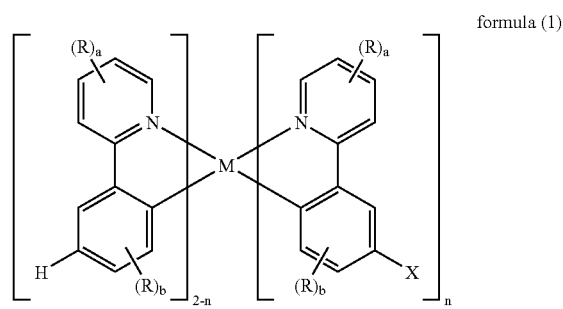

formula (1)

-continued formula (2)

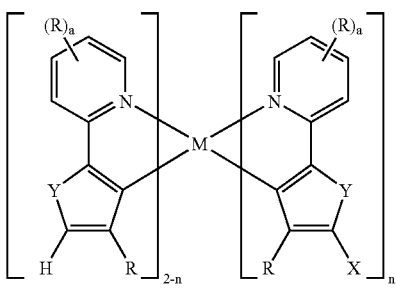

where the symbols and indices are each defined as follows:
M is Pd or Pt;
X is Cl, Br or I;
Y is O, S, Se or $NR^1$;
R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, —$SiR^1{}_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;
$R^1$ are the same or different at each instance and are each H or an aliphatic or aromatic hydrocarbon radical having from 1 to 20 carbon atoms;
a is 0, 1, 2, 3 or 4;
b is 0, 1, 2 or 3; and
n is 1 or 2.

2. A compound of the formula (1a) or (2a)

formula (1a)

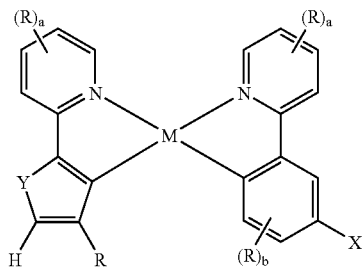

formula (2a)

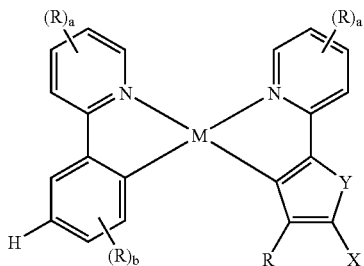

where the symbols and indices are each defined as follows:
M is Pd or Pt;
X is Cl, Br or I;
Y is O, S, Se or $NR^1$;
R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, —$SiR^1{}_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;
$R^1$ are the same or different at each instance and are each H or an aliphatic or aromatic hydrocarbon radical having from 1 to 20 carbon atoms;
a is 0, 1, 2, 3 or 4;
b is 0, 1, 2 or 3.

3. A compound of the formula (3) or (4)

formula (3)

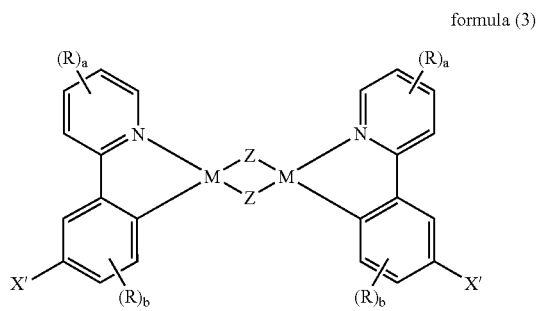

formula (4)

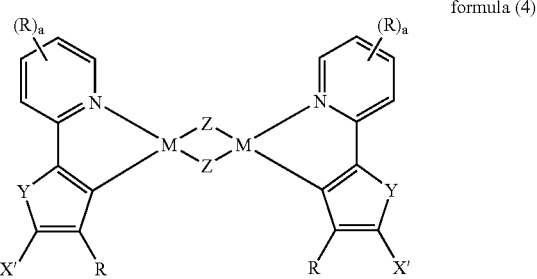

where the symbols and indices are each defined as follows:
M is Pd or Pt;
X' is H, Cl, Br or I, with the proviso that at least one X' per formula is selected from Cl, Br or I;
Y is O, S, Se or $NR^1$;
Z is identically F, Cl, Br, I, O—$R^1$, S—$R^1$ or $N(R^1)_2$;
R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, —$SiR^1{}_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

$R^1$ are the same or different at each instance and are each H or an aliphatic or aromatic hydrocarbon radical having from 1 to 20 carbon atoms;

a is 0, 1, 2, 3 or 4; and b is 0, 1, 2 or 3.

4. A compound of the formula (5), (6), (7) or (8)

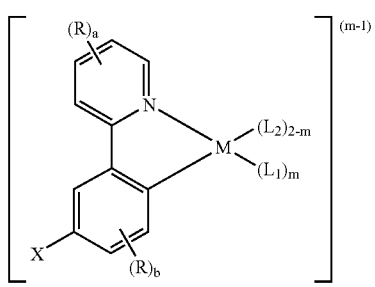

formula (5)

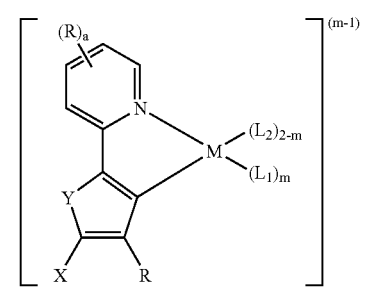

formula (6)

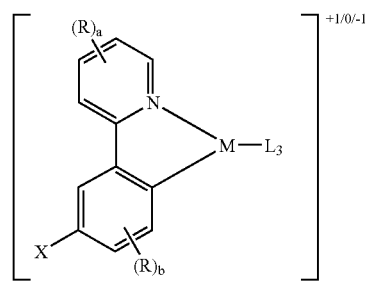

formula (7)

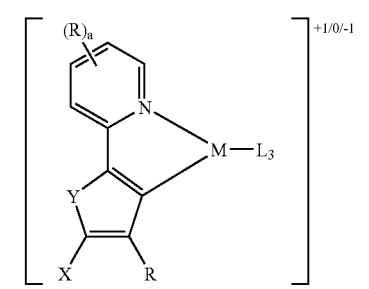

formula (8)

where the symbols and indices are each defined as follows:

M is Pd or Pt;

X is Cl, Br or I;

Y is O, S, Se or $NR^1$;

R is the same or different at each instance and is H, F, Cl, Br, I, $NO_2$, CN, a straight-chain or branched or cyclic alkyl or alkoxy group having 1 to 20 carbon atoms, in which one or more nonadjacent $CH_2$ groups may be replaced by —O—, —$SiR^1{}_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

$R^1$ are the same or different at each instance and are each H or an aliphatic or aromatic hydrocarbon radical having from 1 to 20 carbon atoms;

$L_1$ is an uncharged, monodentate ligand;

$L_2$ is a monoanionic, monodentate ligand;

$L_3$ is an unchanged or mono- or dianionic bidentate ligand;

a is 0, 1, 2, 3 or 4;

b is 0, 1, 2 or 3; and m is 0, 1 or 2.

5. A compound as claimed in claim 4, characterized in that $L_1$ is carbon monoxide, an isonitrile, an amine, morpholine, phosphine, aliphatic, aromatic or heteroaromatic phosphines, phosphate, arsine, stibine, or a nitrogen-containing heterocycle.

6. A compound as claimed in claim 4, characterized in that $L_2$ is a halide, cyanide, cyanate, isocyanate, thiocyanate, isothiocyanate, an alkoxide, methanethiolate, ethanethiolate, propanethiolate, isopropanethiolate, tert-thiobutoxide, thiophenoxide, an amide, a carboxylate, propionate, benzoate, or an anionic nitrogen-containing heterocycle.

7. A compound as claimed in claim 4, characterized in that $L_3$ is a diamine, cis-, trans-diaminocyclohexane, cis-, trans-N,N,N',N'-tetramethyldiaminocyclohexane, imine, diimine, diphosphine, heterocycles containing two nitrogen atoms, 1,3-diketonates derived from 1,3-diketones, 3-ketonates derived from 3-keto esters, carhoxylates derived from aminocarboxylic acids, salicyliminates derived from salicylimines, dialkoxides derived from dialcohols, dithiolates derived from dithiols heteroarylborate.

8. A process for preparing the compounds defined in claim 1, by reacting the compounds (9) or (10)

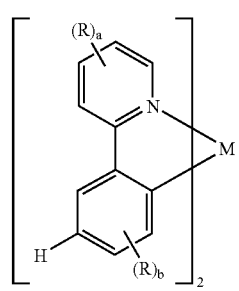

compounds (9)

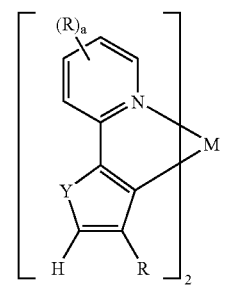

compounds (10)

in which M and the radicals and indices Y, R, $R^1$, a and bare each as defined in claim 1 with halogenating agents and subsequently reducing them.

9. A process for preparing the compounds defined in claim 3, by reacting the compounds (11) or (12)

compounds (11)

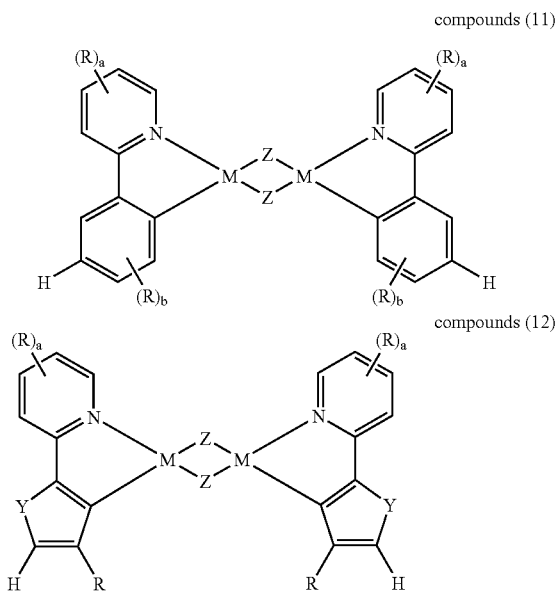

compounds (12)

in which M and the radicals and indices Z, Y, R, R¹, a and b are each as defined in claim 3 with halogenating agents and subsequently reducing them.

10. A process for preparing the compounds defined in claim 4, by reacting the compounds (13), (14), (15) or (16),

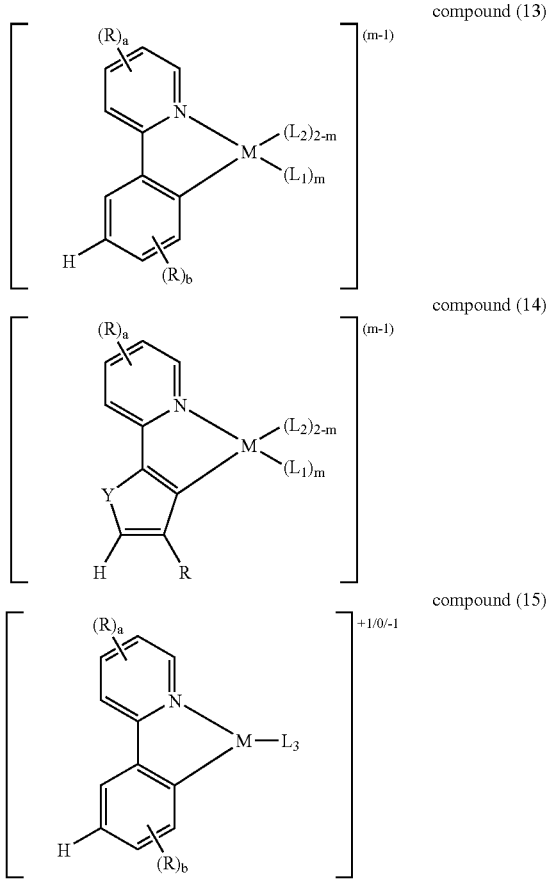

compound (13)

compound (14)

compound (15)

compound (16)

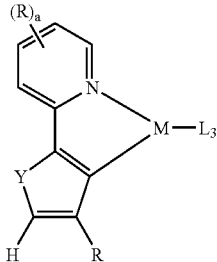

in which M and the radicals and indices $L_1$, $L_2$, $L_3$, Y, R, R¹, a, b and m are each as defined in claim 4, with halogenating agents and subsequently reducing them.

11. The process as claimed in claim 8, characterized in that the halogenating agent used is a halogen $X_2$ or an interhalogen X—X and a base in a molar ratio of from 1:1 to 1:100, or an organic bromine complex such as pyridinium perbromide, and in each case optionally a Lewis acid in a molar ratio (halogen to Lewis acid) of from 1:0.1 to 1:0.0001.

12. The process as claimed in claim 8, characterized in that the halogenating agent used is an organic N-Hal compound.

13. The process as claimed in claim 8, characterized in that the halogenating agent used comprises organic O-Hal compounds and halogens $X_2$ in a molar ratio of from 0.5:1 to 1:1.

14. The process as claimed in claim 11, characterized in that a stoichiometric ratio of the halogenating agents as claimed in claim 11 based on the content of active halogen, to the compounds (9) and (10), of 2:1 is used.

15. The process as claimed in claim 11, characterized in that a stoichiometric ratio of the halogenating agents as claimed in claim 11, based on the content of active halogen, to the compounds (9) and (10), of from 3:1 to 1000:1 is used.

16. The process as claimed in claim 11, characterized in that a reducing agent is added to the reaction mixture in a molar ratio of from 1:1 to 10 000:1 based on the compounds (9) and (10), and the addition is effected simultaneously with the addition of the halogenating agents (I), (II) or (III), or after a time delay.

17. The process as claimed in claim 11, characterized in that the reducing agent used is hydrazine (hydrate) or salts thereof, hydroxylamine or salts thereof, hydroxylamine-O-sulfonic acid and hydroquinones, alkali metal and alkaline earth metal sulfites, alkali metal and alkaline earth metal dithionites, alkali metals and alkaline earth metals and their amalgams and other corresponding alloys, transition metals such as manganese, iron, nickel and zinc, and transition metal alloys.

18. The process as claimed in claim 11, characterized in that the reduction may also be effected by dry-heating, under reduced pressure, the palladium(IV) or platinum(VI) compounds which have been formed as intermediates and isolated in substance.

19. A compound as claimed in claim 1, characterized in that its purity (determined by means of ¹H NMR or HPLC) is more than 99%.

20. A conjugated or semiconjugated or nonconjugated polymer containing one or more compounds of the formula (1') and/or (2')

formula (1')

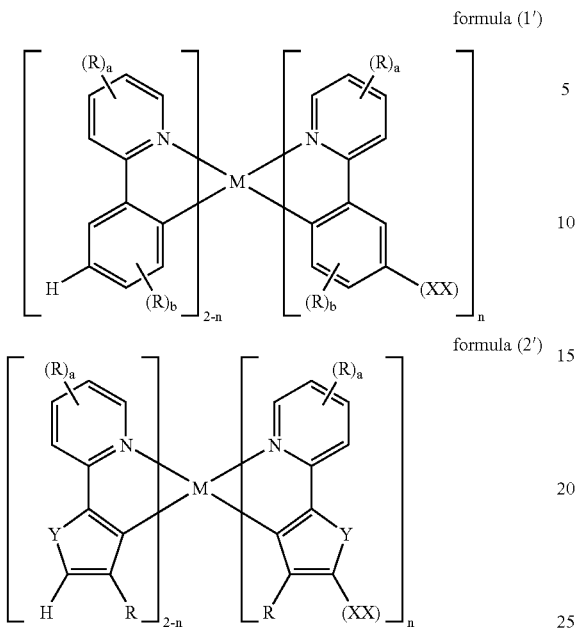

and/or of the formula (1a') and/or (2a')

formula (1a')

formula (2a')

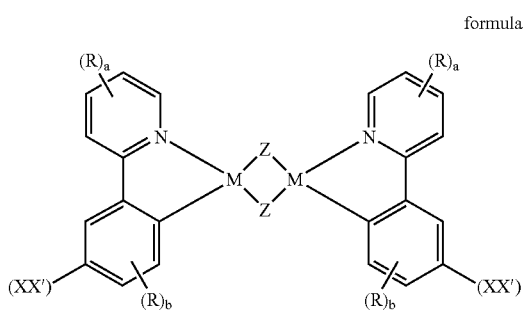

and/or of the formula (3'), (4'), (5'), (6'), (7') and/or (8')

formula (3')

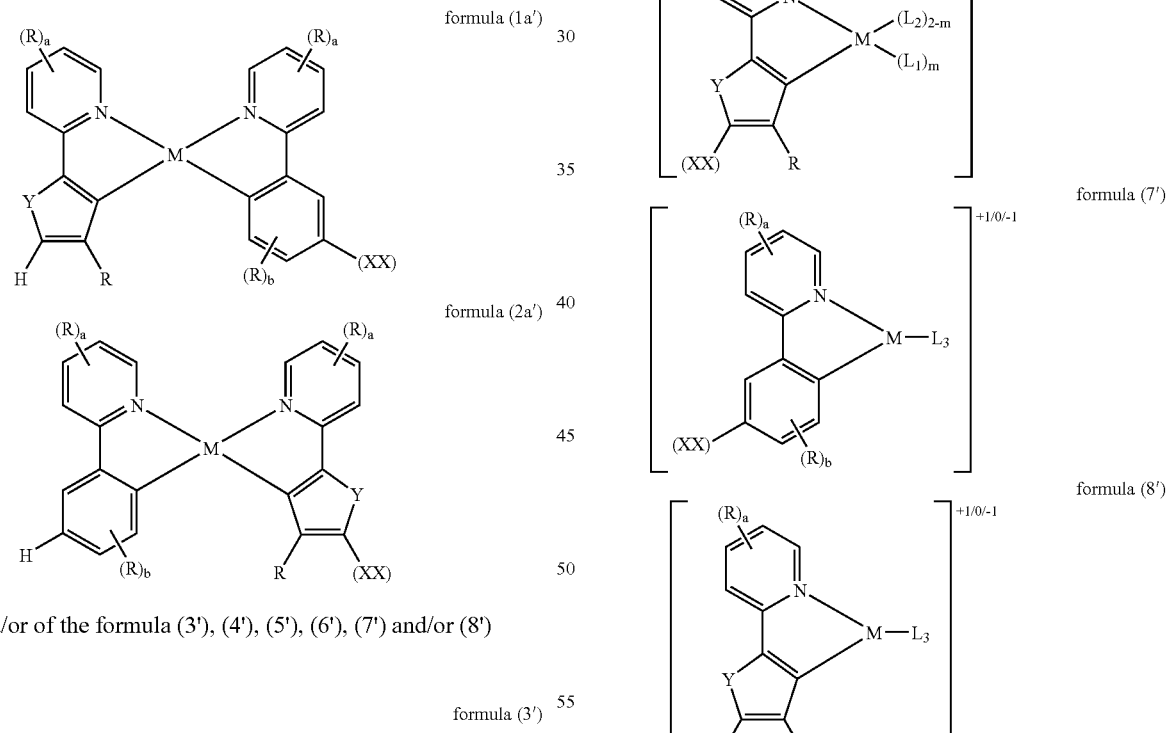

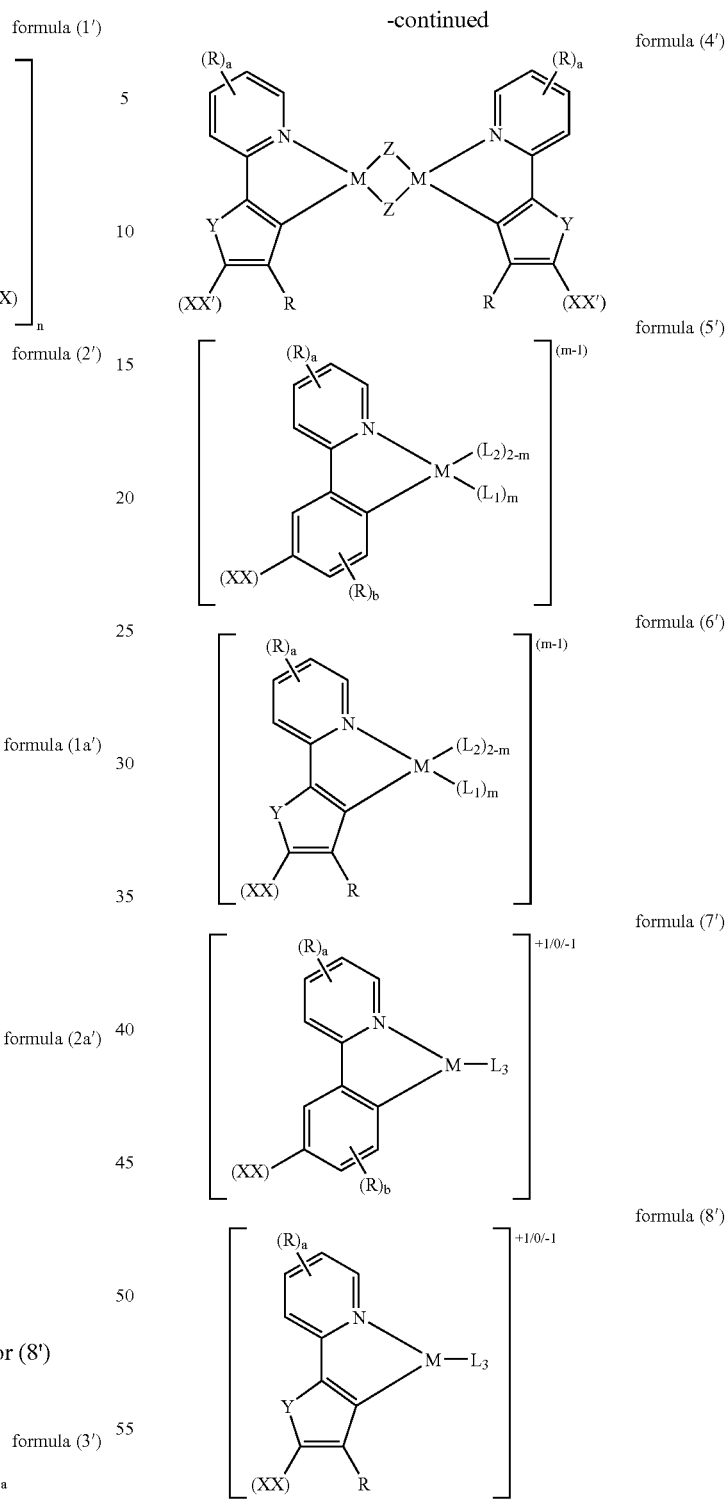

where the symbols and indices are each defined as follows:
M is Pd or Pt;
Y is O, S, Se or NR$^1$;
R is the same or different at each instance and is H, F, Cl, Br, I, NO$_2$, CN, a straight-chain or branched or cyclic alkyl or alkoxy group having 1 to 20 carbon atoms, in which one or more nonadjacent CH$_2$ groups may be replaced by —O—, —SiR$^1_2$—, —S—, —NR$^1$— or —CONR$^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

R$^1$ are the same or different at each instance and are each H or an aliphatic or aromatic hydrocarbon radical having from 1 to 20 carbon atoms;

$L_1$ is an uncharged, monodentate ligand;

$L_2$ is a monoanionic, monodentate ligand;

$L_3$ is an uncharged or mono—or dianionic bidentate ligand;

a is 0, 1, 2, 3 or 4;

b is 0, 1, 2 or 3;

m is 0, 1 or 2;

n is 1 or 2;

(XX) is a bond to the conjugated or semiconjugated or nonconjugated polymer;

(XX') is H or a bond to the conjugated or semiconjugated or nonconjugated polymer, but at least one (XX') per formula is a bond to the conjugated or semiconjugated or nonconjugated polymer.

21. A polymer as claimed in claim 20, characterized in that it has been obtained using one or more compounds of the formula (1), (1a), (2), (2a) and/or (3) to (8)

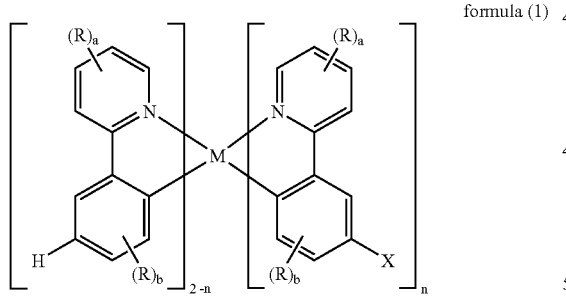

formula (1)

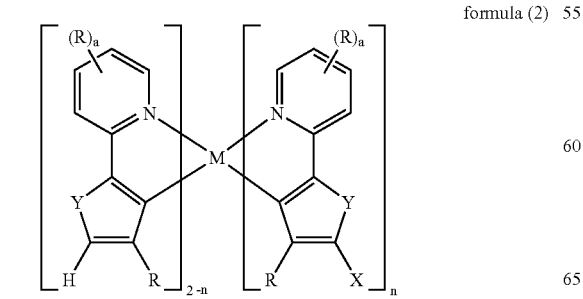

formula (2)

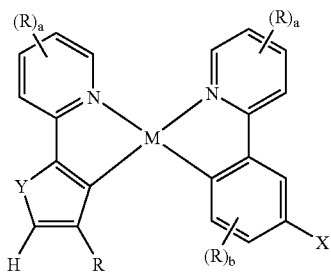

formula (1a)

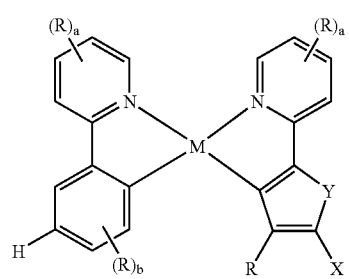

formula (2a)

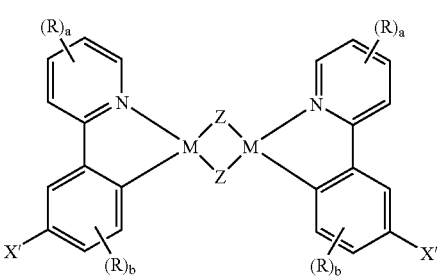

formula (3)

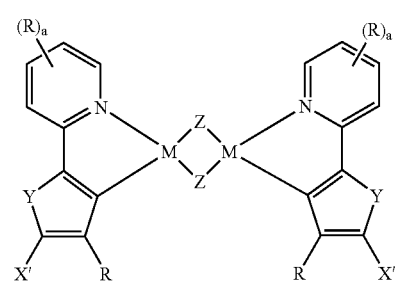

formula (4)

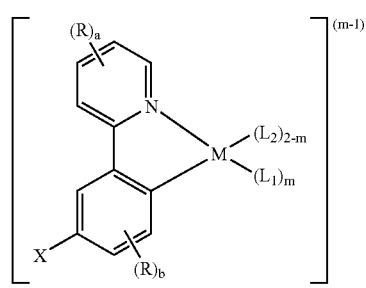

formula (5)

-continued

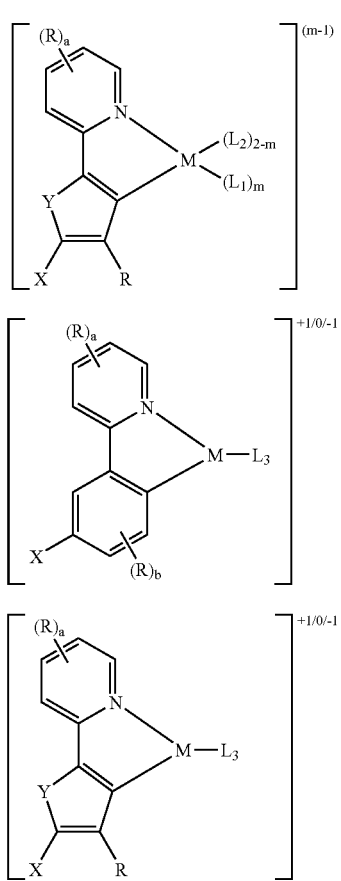

formula (6)

formula (7)

formula (8)

where the symbols and indices are each defined as follows:
M is Pd or Pt;
X is Cl, Br or I;
Y is O, S, Se or NR$^1$;
R is the same or different at each instance and is H, F, Cl, Br, I, NO$_2$, CN, a straight-chain or branched or cyclic alkyl or alkoxy group having 1 to 20 carbon atoms, in which one or more nonadjacent CH$_2$ groups may be replaced by —O—, —SiR$^1$$_2$—, —S—, —NR$^1$— or —CONR$^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;
R$^1$ are the same or different at each instance and are each H or an aliphatic or aromatic hydrocarbon radical having from 1 to 20 carbon atoms;
L$_1$ is an uncharged, monodentate ligand;
L$_2$ is a monoanionic, monodentate ligand;
L$_3$ is an uncharged or mono- or dianionic bidentate ligand;
X' is H, Cl, Br or I, with the proviso that at least one X' per formula is selected from Cl, Br or I;
Z is identically F, Cl, Br, I, O—R$^1$, S—R$^1$ or N(R$^1$)$_2$;
a is 0, 1, 2, 3 or 4;
b is 0, 1, 2 or 3;
m is 0, 1 or 2 and
n is 1 or 2.

22. A polymer as claimed in claim 20 characterized in that the polymer contains repeat units taken from polyfluorenes, polyspirobifluorenes, poly-para-phenylenes, polycarbazoles or polythiophenes.

23. A polymer as claimed in claim 20, characterized in that the polymer is a homo- or copolymer.

24. A polymer as claimed in claim 20, characterized in that the polymer is soluble in organic solvents.

25. An electronic component comprising at least one compound as claimed in claim 1.

26. An electronic component comprising at least one polymer as claimed in claim 20.

27. An electronic component as claimed in claim 25, characterized in that it comprises organic or polymeric light-emitting diodes (OLEDs or PLEDs), organic integrated circuits (O-ICs), organic field-effect transistors (OFETs), organic thin-film transistors (OTFTs), organic solar cells (O-SCs) or else organic laser diodes (O-lasers).

* * * * *